(12) United States Patent
Laufer

(10) Patent No.: US 9,211,154 B2
(45) Date of Patent: Dec. 15, 2015

(54) METHODS AND DEVICES FOR REMOVING OMENTAL TISSUE

(76) Inventor: Michael D. Laufer, Menlo Park, CA (US)

(*) Notice: Subject to any disclaimer, the term of this patent is extended or adjusted under 35 U.S.C. 154(b) by 907 days.

(21) Appl. No.: 13/098,224

(22) Filed: Apr. 29, 2011

(65) Prior Publication Data

US 2012/0277742 A1    Nov. 1, 2012

(51) Int. Cl.
| | |
|---|---|
| A61B 18/08 | (2006.01) |
| A61B 18/14 | (2006.01) |
| A61B 17/30 | (2006.01) |
| A61B 17/3205 | (2006.01) |
| A61B 17/32 | (2006.01) |

(52) U.S. Cl.
CPC ............. *A61B 18/14* (2013.01); *A61B 17/30* (2013.01); *A61B 18/1482* (2013.01); *A61B 17/32056* (2013.01); *A61B 18/1492* (2013.01); *A61B 2017/306* (2013.01); *A61B 2017/320044* (2013.01); *A61B 2018/141* (2013.01)

(58) Field of Classification Search
CPC ............... A61B 18/14; A61B 18/1482; A61B 18/1492; A61B 18/141; A61B 17/30; A61B 17/306; A61B 17/320044; A61B 17/32056
USPC .................... 606/27, 37, 41, 45–52
See application file for complete search history.

(56) References Cited

U.S. PATENT DOCUMENTS

| | | | |
|---|---|---|---|
| 5,312,332 A | 5/1994 | Bales et al. | |
| 5,792,139 A * | 8/1998 | Chambers et al. | 606/41 |
| 6,258,083 B1 * | 7/2001 | Daniel et al. | 606/15 |
| 2006/0259035 A1 * | 11/2006 | Nezhat et al. | 606/50 |
| 2007/0051380 A1 * | 3/2007 | Pasricha | 128/898 |
| 2008/0249553 A1 * | 10/2008 | Gruber et al. | 606/171 |
| 2009/0275842 A1 * | 11/2009 | Saadat et al. | 600/478 |
| 2010/0210999 A1 * | 8/2010 | Laufer | 604/28 |

* cited by examiner

*Primary Examiner* — Ronald Hupczey
*Assistant Examiner* — Eunhwa Kim
(74) *Attorney, Agent, or Firm* — Levine Bagade Han LLP

(57) ABSTRACT

The invention relates to a method of treating obesity, insulin resistance and co-morbidities of these conditions by removing tissue from the abdomen. More specifically, it relates to a method of removing abdominal fat and omentum to which the fat is attached, in order to improve health. The invention includes a device for safely removing this tissue material

21 Claims, 13 Drawing Sheets

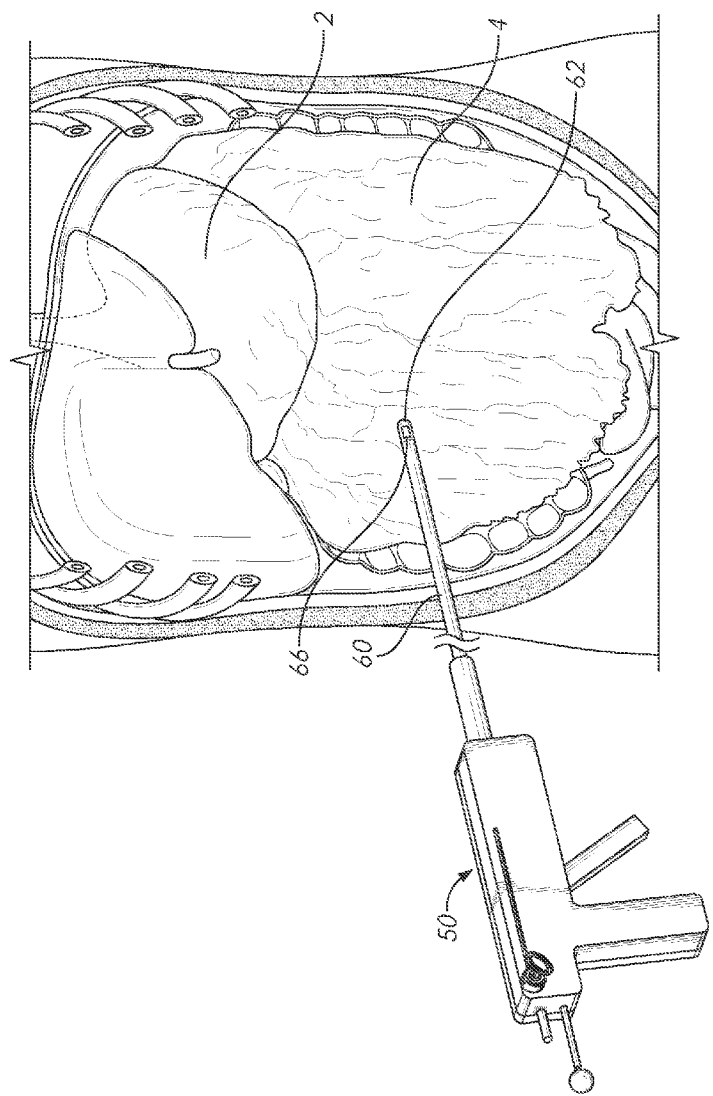

METHODS AND DEVICES FOR REMOVING OMENTAL TISSUE

FIELD OF THE INVENTION

The invention relates to a method of treating obesity, insulin resistance and co-morbidities of these conditions by removing tissue from the abdomen. More specifically, it relates to a method of removing abdominal fat and omentum to which the fat is attached, in order to improve health. The invention includes a device for safely removing this tissue material.

BRIEF DESCRIPTION OF THE RELATED ART

The number of obese and morbidly obese people in the US has grown to 70 million in 2006, of which 10 million are morbidly obese (BMI>40). It is expected that this number will grow to 90 million by 2012. Along with direct deleterious effects, obesity also gives rise to other co-morbidities, the most significant being Type II diabetes (24 million in the US, an increase from 12 million 10 years ago), heart and circulatory disease, including peripheral vascular and stroke.

As discussed below, it is believed that there is a direct connection between abdominal fat and type II diabetes. Although obesity and abdominal fat are closely linked, the ratio between abdominal fat and other body fat is a more important indicator of type II diabetes and other morbidities from hormonally-active fat.

Conventional methods for treating obesity include drugs, dieting and surgery. For many patients, short term dietary changes do not result in long term weight loss. This leads many patients to select surgery, especially those patients with significant morbidity related to obesity. In 2004, the Centers for Medicare & Medicaid Services ("CMS") decided to reimburse bariatric surgery. This decision contributed to an already fast-growing rate of obesity surgery: up from 19,000 in 1998 to over 220,000 in 2006. Average reimbursement per case is approximately $25,000, with significant additional expense to treat follow-on issues, such as infection and gastric problems.

Current methods and devices for removing omentum and fat require either open surgery with large incisions or can be done with difficulty using laparoscopic techniques. However, the current procedures require painstaking cauterization of the blood vessels contained within this tissue material and careful excision. Frequently, the procedure is complicated by bleeding in the area of the tissue removal, requiring prolonged hospitalization and/or reoperation. The complications from bleeding limit the procedure to rare occasions and is only performed by particularly skilled surgeons.

Omentectomy (removal of the omentum and fat) is currently reimbursable but not often done. This may be due in part to the complexity and surgical risks inherent in these operations. These are compounded by the need for prolonged general anesthesia and immobility before and after the surgery.

Removing omental fat from the middle of the abdomen is significant in at least two ways: (1) omental fat is a primary contributor to Type II diabetes, and (2) omental fat contributes to coronary artery disease and other co-morbidities of obesity. Even moderately obese patients with larger abdominal girth are at higher risk for comorbidities like hypertension, diabetes and arterial vascular disease. Abdominal fat remains behind even after significant weight loss and continues to add risk to these patients. Only by removing this abdominal fat can these problems be directly addressed. Abdominal fat is the single largest factor in determining insulin resistance and an atherogenic lipid profile. It is believed that removing abdominal fat can reduce both diabetes (due to insulin resistance) and arterial sclerosis (due to lipogenic atheroma). Reducing arterial sclerosis can lead to a reduction of stroke, hypertension and peripheral arterial disease.

It has been found in a number of human studies that the presence of omental fat has a higher correlation with the production of dyslipidemia, hypertension, congestive heart failure and inflammatory response than the usual measures of obesity, such as BMI (Body Mass Index).

This correlation has been established by substantial animal testing, epidemiological studies relating visceral (omental) fat with metabolic, hormonal and vascular disorders, and with Type II diabetes. There are a number of studies currently underway, but the largest study compared bariatric surgery (Lap Band) with bariatric surgery and omentum removal (A Thörne, 2002). This study was performed on 50 patients. While all received an adjustable gastric band (AGB) for gastric reduction, half (n=25) additionally had a portion of their fatty omentum removed. The total amount removed was small—only 0.8% of total body fat (which amounts to only about 1 pound for a 300-pound person with a BMI of 40).2 Despite the relatively small amount of fat removed, the omentectomized patients recorded significant reductions in oral glucose tolerance and insulin sensitivity-2 to 3 times greater than control subjects (P=0.009 to 0.04). The authors concluded:

Omentectomy, when performed together with AGB, has significant positive and long-term effects on the glucose and insulin metabolic profiles in obese subjects (A Thörne, 2002).

Multiple published articles are included in this application and are included here by reference. A Thörne, F Lönnqvist, J Apelman, G Hellers and P Arner. "A pilot study of long-term effects of a novel obesity treatment: omentectomy in connection with adjustable gastric banding." International Journal of Obesity 26.2 (2002): 193-199; Adams, M. The truth on losing abdominal body fat—forget the diet hype, here's how it really works. 18 Apr. 2005. 24 Sep. 2008 <<http://www.naturalnews.com/z006981.html>>; Brochu, M, Starling, RD, Tchernof, A, Matthews, D E, Garcia-Rubi, E and Poehlman, E T. "Visceral Adipose Tissue Is an Independent Correlate of Glucose Disposal in Older Obese Postmenopausal Women." The Journal of Clinical Endocrinology & Metabolism (2000): 2378-2384; Brower, B G, Visseren, FLJ, Stolk, R P and van der Graaf, Y; "Abdominal Fat and Risk of Coronary Heart Disease in Patients with Peripheral Arterial Disease*." Obesity (2007): 1623-1630; Cid Pitombo1, Eliana P Araújo, Cláudio T De Souza, José C Pareja, Bruno Geloneze and Licio A Velloso. "Amelioration of diet-induced diabetes mellitus by removal of visceral fat." Journal of Endocrinology (2006): 699-706; C V Ferchak, L F Meneghini. "Obesity, bariatric surgery and type 2 diabetes—a systematic review." Diabetes Metabolism Research and Reviews (2004): 438-445; Després, J-P, Lemieux, I, Prud'homme, D. "Treatment of obesity: need to focus on high risk abdominally obese patients." British Medical Journal (2001): 716-720; Flegal K, Carroll M, Kuczmarski R, et al. "Overweight and obesity in the United States: prevalence and trends, 1960-1994." Int J Obes Relat Metab Dis. (1998): 39-47; Gabriely, I, Ma, X H, Yang, X M, Atzmon, G, Rajala, M W, Berg, A H, Scherer, P, Rossetti, L and Barzlai, N. "Removal of Visceral Fat Prevents Insulin Resistance and Glucose Intolerance of Aging." Diabetes (2002): 2951-2958; Gan, S K, Kriketos, A D, Poynten, A M, Furler, S M, Thompson, C H, Kraegen, E W, Campbell, L V and Chisholm, D J. "Insulin Action, Regional Fat, and Myocyte Lipid: Altered Relationships with Increased Adiposity." Obesity Research (2003): 1295-1305; Gaudet, G., Vohl, M-C, Perron, P, Tremblay, G, Gagné, C, Lesiège, D, Bergeron, J, Moorjani, S, Després, J-P. "Relationships of Abdominal Obesity and Hyperinsulinemia to Angiographically Assessed Coronary Artery Disease in Men With Known Mutations in the LDL Receptor Gene." Circulation (1998): 871-877; Goldberg, C. "'Visceral' fat removal prompts hope." Boston Globe 17 Apr. 2004: n.p. 13. Gower, B A, Munoz, J, Desmond, R, Hilario-Hailey, T and Jiao, X. "Changes in Intra-abdominal Fat in Early Postmenopausal Women: Effects of Hormone Use." Obesity Research (2006): 1046-1055; Hamdy, O. "The Role of Adipose Tissue as an Endocrine Gland." Current Diabetes Reports (2005): 317-319; Janssen, I., Katzmarzyk, PT, Ross, R, Leon, A S, Skinner, J S, Rao, D C, Wilmor, J H, Rankinen, T and Bouchard, C. "Fitness Alters the Associations of BMI and Waist Circumference with Total and Abdominal Fat**." Obesity Research (2004): 525-537; Kelley, D E and Goodpaster, B H. "Review Article, Skeletal Muscle Trigliceride, an Aspect of Regional Adiposity and Insulin Resistance." Diabetes Care (2001): 933-941; Lemieux, I, Pascot, A, Couillard, C, Lamarche, B, Tchernof, A, Almeras, N, Bergeron, J, Gaudet, D, Tremblay, G, Prud'homme, D, Nadeau, A and Despres, J-P. "Hypertrigyceridemic Waist: A Marker of the atherogenic metabolic triad (hyperinsulinemia; hyperapoliprotein B; Small, dense LDL) in Men?" Circulation (2000): 79; Mass General Hospital. "Growth Hormone Reduces Abdominal Fat, Cardiovascular Risk in HIV Patients on Antiviral Therapy." ScienceDaily 6 Aug. 2008: n.p; Moghaddam, E, Vogt, J A and Wolever, TMS. "The Effects of Fat and Protein on Glycemic Responses in Nondiabetic Humans Vary with Waist Circumference, Fasting Plasma Insulin, and Dietary Fiber Intake1." American Society for Nutrition (2006): 2506-2511; Norstrom, A, Neovius, M G, Rossner, S and Nordstrom, P. "Postpubertal Development of Total and Abdominal Percentage Body Fat: An 8-Year Longitudinal Study." Obesity (2008): n.p; O'Connor, K G, et al. "Interrelationships of spontaneous growth hormone axis activity, body fat, and serum lipids in healthy elderly women and men." Metabolism, Clinical and Experimental (1999): 1424-1431; Pedersen S B, Børglum J D, Schmitz O, Bak J F, Sørensen N S, Richelsen B. "Abdominal obesity is associated with insulin resistance and reduced glycogen synthetase activity in skeletal muscle." Metabolism (1993): 998-1005; Pitombo, C, Araujo, E P, DeSouza, C T, Parja, J C, Beloneze, B and Velloso, L A. "Amelioration of diet-induced diabetes mellitus by removal of visceral fat." Journal of Endocrinology (2006): 699-706; Pontiroli A Pizzocri P, Librenti M. "Laparascopic adjustable gastric banding for the treatment of morbid (grade 3) obesity and its metabolic complications: a three-year study." J. Clin. Endocrinol. Metab. (2002): 3555-3561; Pories W J, Swanson M S, MacDonald KG, et al. "Who would have thought it? An operation proves to be the most effective therapy for adult-onset diabetes mellitus." Ann Surg (1995): 339-352; Schauer, P R. "Effect of Laparoscopic Roux-En Y Gastric Bypass on Type 2 Diabetes Mellitus." Annals of Surgery (2003): 467-485; Shi, H, Strader, A D, Woods, S C and Seeley, R J. "The effect of fat removal on glucose tolerance is depot specific in male and female mice." American Journal of Physiology and Endocrinological Metabolism (2007): 1012-1020; Sjostrom C, Lissner L, Wedel H, et al. "Reduction in incidence of diabetes, hypertension and lipid disturbances after intentional weight loss induced by bariatric surgery: the SOS Intervention." Obes. Res. (1999): 477-484; Soodini, G R and Hamdy, O. "Obesity and Endothelial Function, Obesity and Nutrition." Current Opinion in Endocrinology & Diabetes (2004): 186-191; Thörne, A, Lönnqvist, F, Apelman, J, Hellers, G and Amer, P. "A pilot study of long-term effects of a novel obesity treatment: omentectomy in connection with adjustable gastric banding." International Journal of Obesity (2002): 193-199; Vega, G L, Adams-Huet, B, Peshock, R, Willet, D, Shah, B and Grundy, S M. "Influence of Body Fat Content and Distribution on Variation in Metabolic Risk." The Journal of Clinical Endocrinology & Metabolism (2006): 4459-4466; Yeager, J A Florence and BF. "Treatment of Type 2 Diabetes Mellitus." American Family Physician (1999): 2049; and Yeckel, C W, Dziura, J and DiPietro, L. "Abdominal Obesity in Older Women: Potential Role for Disrupted Fatty Acid Reesterification in Insulin Resistance." Journal of the Clinical Endocrinology and Metabolism (2008): 1285-1291.

There remains a need to effectively and safely remove large amounts of omentum while addressing the risks associated with highly vascularized hormonally active tissue.

SUMMARY OF THE INVENTION

The present invention pertains to the use of a laparoscopic and/or a natural orifice surgery ("NOSCAR") procedure to remove large amounts of omental fat from within the abdomen while addressing the complications that often arise from the highly vascularized omentum tissue that leads to excessive bleeding. In one variation, the method and system comprise a series of disposable elements that are deployed with or through an endoscope or laparoscope, primarily for securing sections of omental fat tissue, sealing the blood vessels to prevent bleeding. The system and method can include performing the procedure through a natural orifice such as the nose or mouth. In such a case, the procedure creates an opening in the stomach (thereby leaving no external visible scar). Then sections of omentum are then excised and brought into the stomach for removal. In additional variations, the omentum is drawn into the stomach and then a device is used to extract the section of omentum while cauterizing or coagulating vessels in the remaining omentum section to stem bleeding. The omentum can be macerated and evacuating from the stomach or from the abdominal cavity. One significant benefit is that the removal of significant amounts of omentum in such a minimally invasive manner provide for direct and immediate weight loss (up to 30 pounds). Moreover, because the omentum is hormonally active tissue or fat, removing this tissue from the body can reduce the incidence of morbidity from diabetes, heart disease and stroke, in obese patients. The removed omental fat can also be used for other procedures (i.e. cosmetic), as it has been shown to be more permanent than injected liposuction fat. More importantly, removal of this tissue from the body during the procedure eliminates the collateral effects of leaving the hormonal omental tissue within the body (as in such cases where the omental tissue is treated, ablated, or otherwise inactivated.).

In one variation, the systems and methods described herein focuses on removing omentum and omental fat (hereafter either or both being referred to as "omental tissue") from the middle of the abdomen. Such removal can occur in an open procedure, or a minimally invasive procedure.

The methods and devices described herein permit removal of large amounts of omental fat while performing a minimally invasive and/or scar-less procedure. Moreover, the ability to secure and coagulate the omentum tissue (omentum and the omental fat) reduces the incidence of bleeding lowering the difficulty of the procedure. The ability to remove large amounts of omentum tissue also provides immediate weight loss and sculpting like liposuction.

The methods described herein include removing a portion of omentum tissue from a human body. The methods can be performed via open surgical procedures, through ports or openings in the outer abdominal wall, and/or through natural body openings such as the nose, mouth, etc.

In one variation, the method includes drawing a portion of the omentum tissue from an abdominal cavity through an incision in the body to secure the portion of omentum; separating the portion of omentum tissue from the human body while cauterizing or coagulating the portion of omentum tissue to reduce bleeding; removing the separated portion of omentum tissue from the body.

As discussed herein, separating and cauterizing or coagulating can occur simultaneously. By doing so, the physician can address the excessive bleeding risks associated with the highly vascularized omentum tissue.

Drawing of the omentum tissue through the incision can be performed mechanically, or using a vacuum-assisted grasper.

The methods include making the incision in an outer abdominal wall of the body or through internal organs. In the latter case, the incision in the internal organ should allow for accessing the abdominal cavity without creating excessive or any external scars. In one such example, drawing the portion of the omentum tissue through the incision comprises advancing an access device into a stomach of the body, creating the incision in the stomach and advancing a tissue retrieval device through the incision to draw the portion through the incision. In any case, the procedure can include the use of any number of trocars, access ports, or access catheters to facilitate passage of the devices through the incision.

The procedures described herein can be performed blindly or under direct or indirect visualization. For example, the methods can include placing a visualizing device into the abdominal cavity.

In order to facilitate separation and removal of the omentum tissue, the methods can include placing the portion of omentum tissue in a state of traction.

Although the disclosure discusses creation of an incision through the stomach, the method can include creation of an incision through any accessible organ within the abdominal cavity. For example such organs can include the colon, uterus, small intestine and large intestine.

In addition to the removal of omental tissue, the methods and devices described herein can also remove other tissues. For example, the methods and devices can remove abdominal fat, visceral fat, and abnormal tissue through the incision.

The methods described herein include methods of removing a portion of omentum tissue from a human body. In one variation, the method includes securing the omentum tissue to a shaft; rotating the shaft to affix a portion of omentum tissue about the shaft; separating the omentum tissue from the human body while the portion of omentum tissue is affixed to the shaft; and removing the portion of omentum tissue from the body.

The methods can further include drawing a vacuum through an opening in the shaft to temporarily secure the omentum tissue about the opening. In some cases rotating the shaft to affix the portion of omentum tissue about the shaft further includes placing the portion of omentum tissue in a state of traction.

In some variations the method includes creating an incision in the body and where removing the portion of omentum from the body comprises removing the portion of the omentum through the incision. In other variations, the incision is made in an organ selected from the group consisting of the colon, uterus, small intestine and large intestine.

Separating the omentum tissue from the human body can optionally comprise applying energy to the portion of omentum tissue to cauterize or coagulate the portion of omentum tissue to reduce bleeding. One possible way of performing this is to apply energy to the portion of omentum tissue comprises advancing a loop electrode around the portion of omentum tissue and energizing the loop electrode to separate the omentum tissue. The energy source can be selected from the group consisting of RF energy, coherent light, incoherent light, resistive heat, compressed gas, cooling fluid.

In certain examples, securing the omentum tissue to a shaft occurs as the shaft beings rotating. Securing can occur via any number of ways. For example, in one variation rotating the shaft causes a vacuum source to draw a vacuum through an opening in the shaft to pull the omentum tissue within the opening.

In another variation, the method can include advancing an access device into a stomach of the body, creating an incision in the stomach and removing the portion of omentum from the body through the incision. The incision can be created in an abdominal wall and removing the portion of omentum from the incision in the abdominal wall.

The omentum tissue can be disposed of by morselizing the portion of omentum tissue after or during separating the omentum tissue from the body. While, separating the portion of omentum tissue can be performed by a process selected from the group consisting of heating, mechanically cutting and electrically cutting the portion of tissue.

In alternative variations the method includes drawing the portion of omentum tissue by advancing a retrieval device through the incision, where the retrieval device comprises a distal end, securing the portion of omentum tissue to the distal end and at least partially drawing the portion of omentum tissue into the distal end.

Abdominal fat, visceral fat, and abnormal tissue can be removed through the incision.

The present disclosure also includes an omentum removal device coupleable to a vacuum source, the omentum removal device comprising a shaft coupled to a handle, and having at least one vacuum channel terminating at a tissue receiving opening in a distal portion of the shaft, the shaft being rotatable relative to the handle; a valve coupling the vacuum source to the vacuum channel, where rotation of the shaft causes the valve to open to permit the vacuum source to pull a vacuum through the both vacuum channel and the tissue receiving opening, where rotation of the shaft and drawing of the vacuum causes tissue to be drawn into the tissue receiving opening and wrapped about the shaft; and a tissue cutting member being configured to slidably advance over the shaft tissue wrapped thereon and configured to separate the wrapped tissue from a body of the patient.

In one variation, the device includes a tissue cutting member that comprises a snare comprising a wire-type member forming a loop shape, and further comprising an actuator member coupled to the handle, where the actuator member is capable of reducing a size of the loop shape.

In an additional variation, the device can comprise a trigger member having a pinion member and where a rack member is coupled to a helical groove in the shaft such that movement of the rack member causes rotation of the shaft, where actuator of the trigger member causes rotation of the shaft.

Variations of the devices and procedures described herein include combinations of features of the various embodiments or combination of the embodiments themselves wherever possible.

BRIEF DESCRIPTION OF THE DRAWINGS

The invention will now be described in greater detail with reference to the embodiments illustrated in the accompanying drawings, in which like elements bear like reference numerals and wherein:

FIGS. 9A to 9E show one example of an omentum removal device, such as the variation shown in FIG. 7A, placed into or against omentum tissue and actuated to remove the tissue from the body.

DETAILED DESCRIPTION OF VARIOUS EMBODIMENTS

Figure 1A:
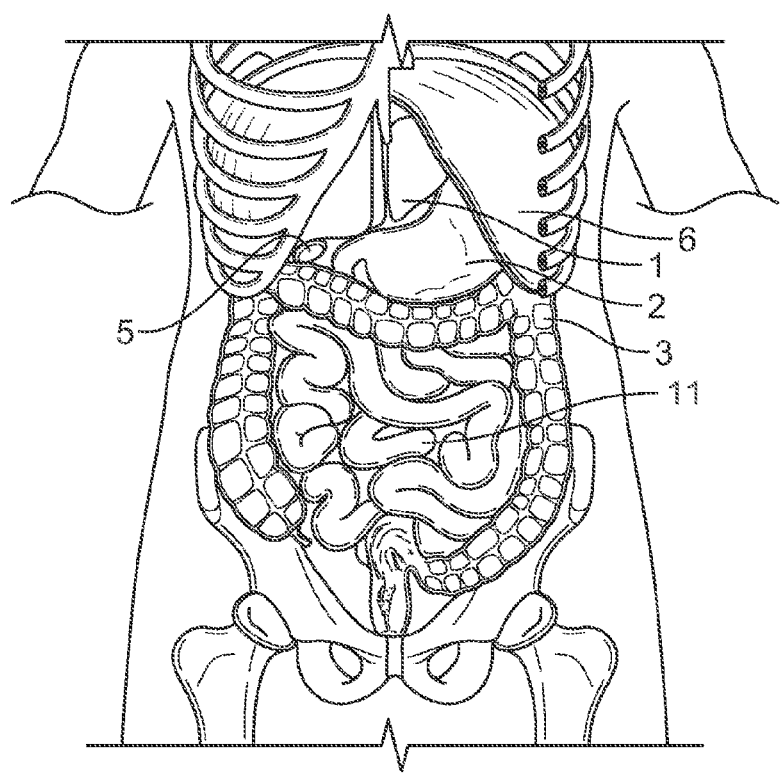
FIG. 1A illustrates an example of an abdominal cavity and abdominal organs.
Figure 1B:
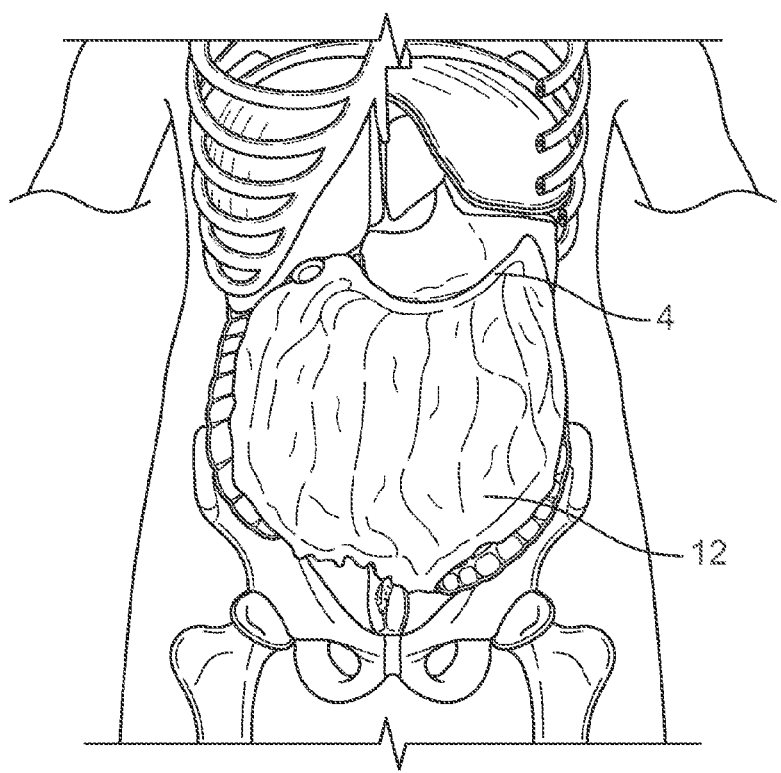
FIG. 1B illustrates an example of the omentum covering organs in the abdominal cavity.

FIG. 1A illustrates an example of an abdominal cavity and abdominal organs (including the liver 1, stomach 2, large intestines 3 and small intestines 11, as well as the gall bladder 5). As shown, the organs are located under the diaphragm 6. For purposes of illustration, the omentum and omental fat are not illustrated in the figure. However, FIG. 1B illustrates the omentum 4 and omental fat 12 which surround the abdominal organs.

Figure 2:
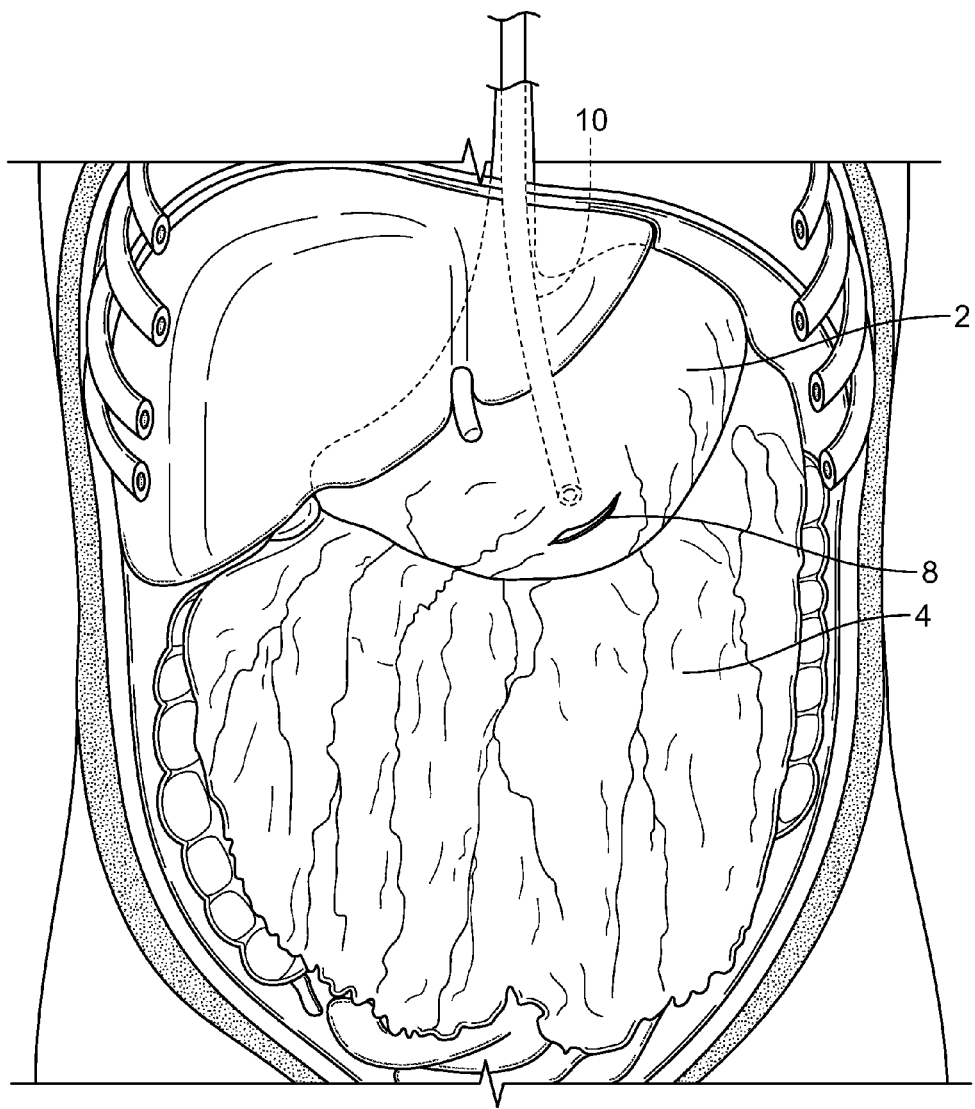
FIG. 2 illustrates the advancement of a device into the stomach to provide access to the abdominal cavity and omentum through an incision in the stomach.

In one variation, the methods described herein allow the surgeon to access the omentum and omental fat through a NOSCAR keyhole through the stomach wall. In doing so, an endoscope or other catheter can be introduced through the mouth for advancement into the stomach. The physician then makes an incision in the stomach or esophagus to enter the abdominal cavity. For example, as shown in FIG. 2, a process of removing portions of the omentum and omental fat uses a path through the stomach 2. As shown, a device 10 such as a scope or other catheter can be advanced through a natural orifice and into the stomach 2. Once inside the stomach 2 cavity, an incision or opening 8 can be made in the stomach wall to expose the omentum 4. The size of the opening 8 in the illustration is for exemplary purposes only as the size can vary as needed. The patient can be sedated, or under general anesthesia depending upon the preference of the physician and the duration of the procedure.

Figure 3A:
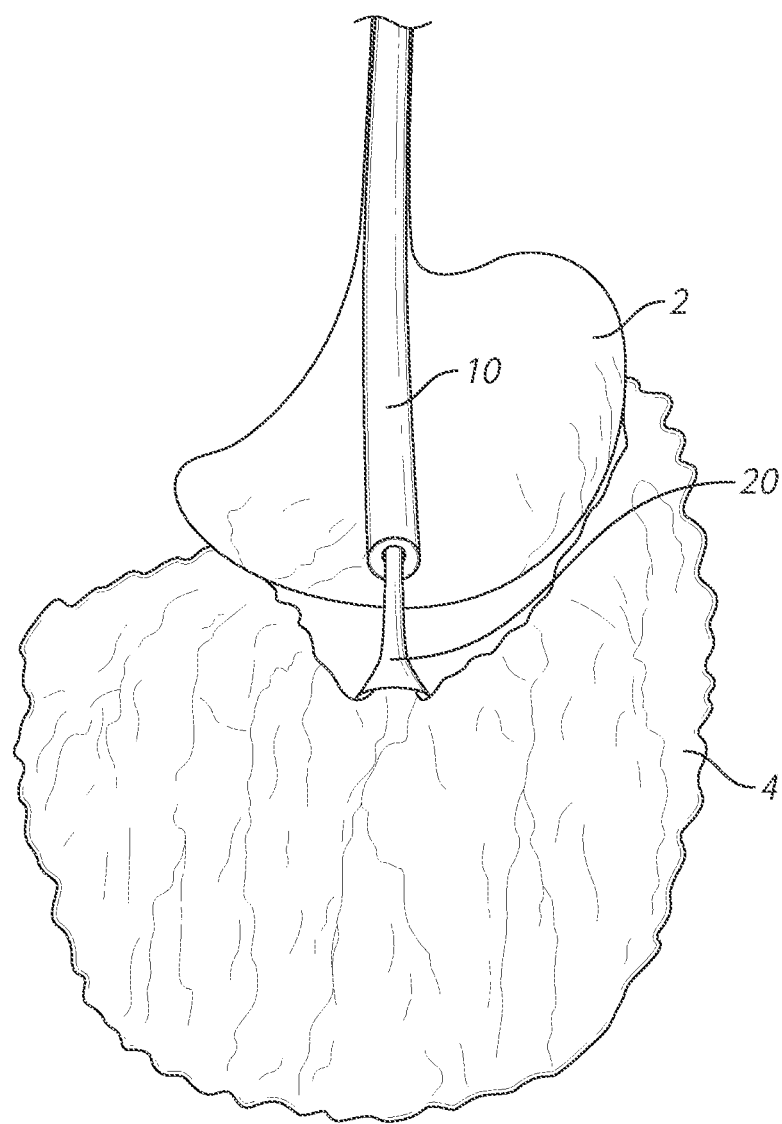
FIG. 3A illustrates an example of an omentum retrieval device advanced through an opening in the stomach to accumulate omentum tissue for resection.
Figure 3B:
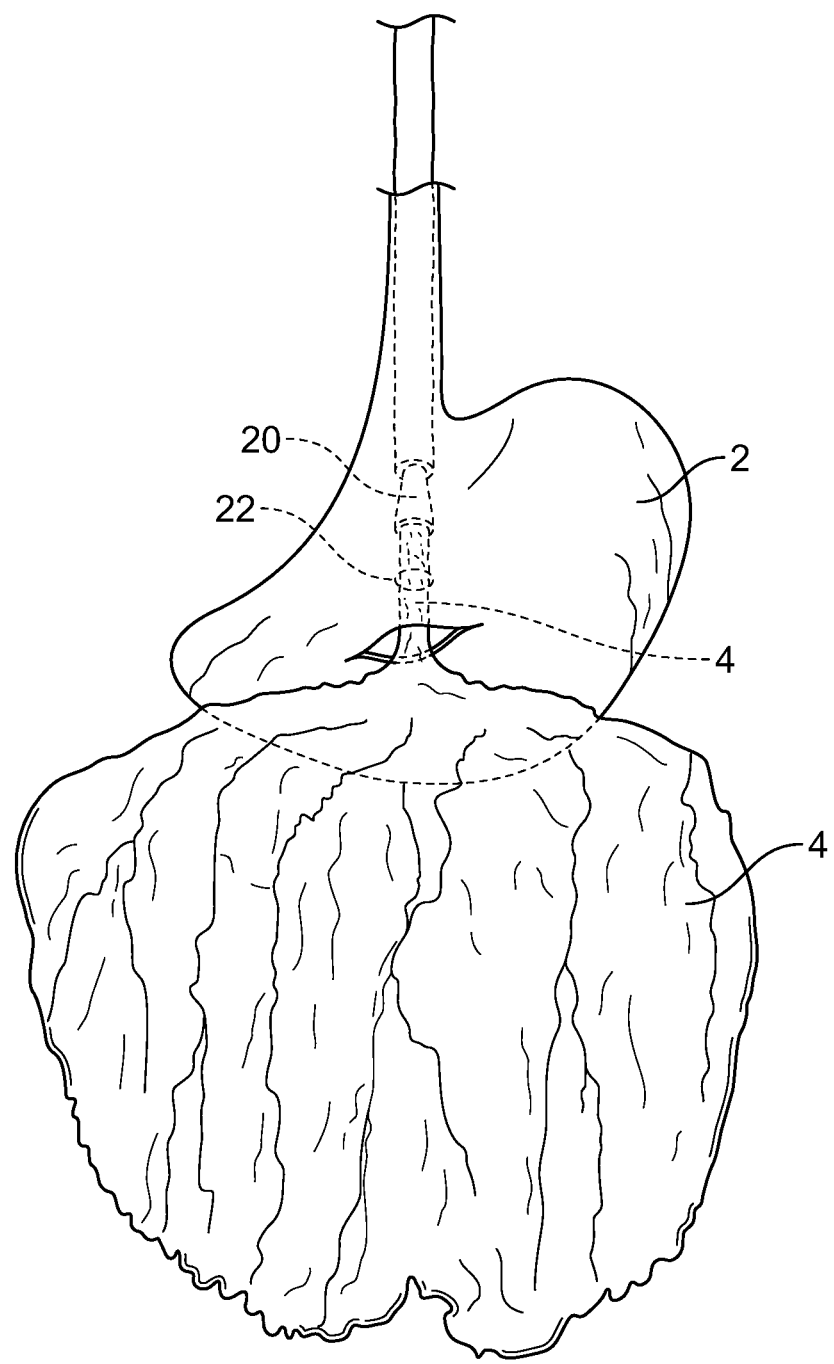
FIG. 3B illustrates withdrawing the omentum into the stomach for removal of the tissue.

Once the abdomen is accessible (i.e., via an opening in the stomach, a port that provides access to the abdomen, or via an open surgical procedure), the physician inserts a device 20 to secure the omentum 4 and omental fat. As shown in FIG. 3A, suction can be used to secure the omentum to the device 20. The cone-shaped tip compresses/groups the omentum 4 as it secures the tissue. Next, the device 20 can be withdrawn into the stomach 2 thereby pulling the omentum 4 into the stomach as shown in FIG. 3B where it can be separated from the remaining omentum tissue and where the vessels in the severed omentum tissue can be cauterized or coagulated. In the illustrated variation, an electrosurgical loop 22 is advanced over the device 20 so that a cutting loop encircles the compressed and drawn omentum 4. The electrosurgical loop is then activated to sever the omentum 4 as well as coagulate any open blood vessels. The omentum debris is then aspirated through the device and retained for further use, or disposed. In any event, the severed omentum tissue is removed from the body. In an alternative variation, the omentum tissue can be severed from the remaining omentum portion outside of the stomach.

In one variation of the methods and system, the distal end of the omentum retrieval/securing device 20 comprises an expandable shape. Therefore, the device 20 is capable of being inserted through the lumen of a laparoscopic introducer such as an 8 mm introducer, or though the working channel of an endoscope. After introduction, through hole having a minimum dimension to accommodate the device 20, the distal end of the device 20 expands improve its ability to draw tissue into the device for removal from the body.

Although the above example shows an electrosurgical means for severing and coagulating, any similar device can be employed. For example, the tissue securing device can include heating to seal the blood vessels using radiofrequency energy, lower frequency electrical energy, resistive heating, compression, freezing, cooling, a combination of any of these. Moreover, such coagulation modes can be combined with mechanical cutting, grinding, and/or shredding to remove the omentum tissue.

As noted herein, while variations of the method and system include accessing the abdominal cavity via the stomach, the methods can be supplemented by the use of one or more ports in an abdominal wall. Alternatively, the procedure can take place entirely via ports in the abdomen. In any case, in these variations, the procedure is performed without leaving any long skin incisions. However, additional variations of the method also include removal of the omental fat via an open surgical procedure.

Figure 4:
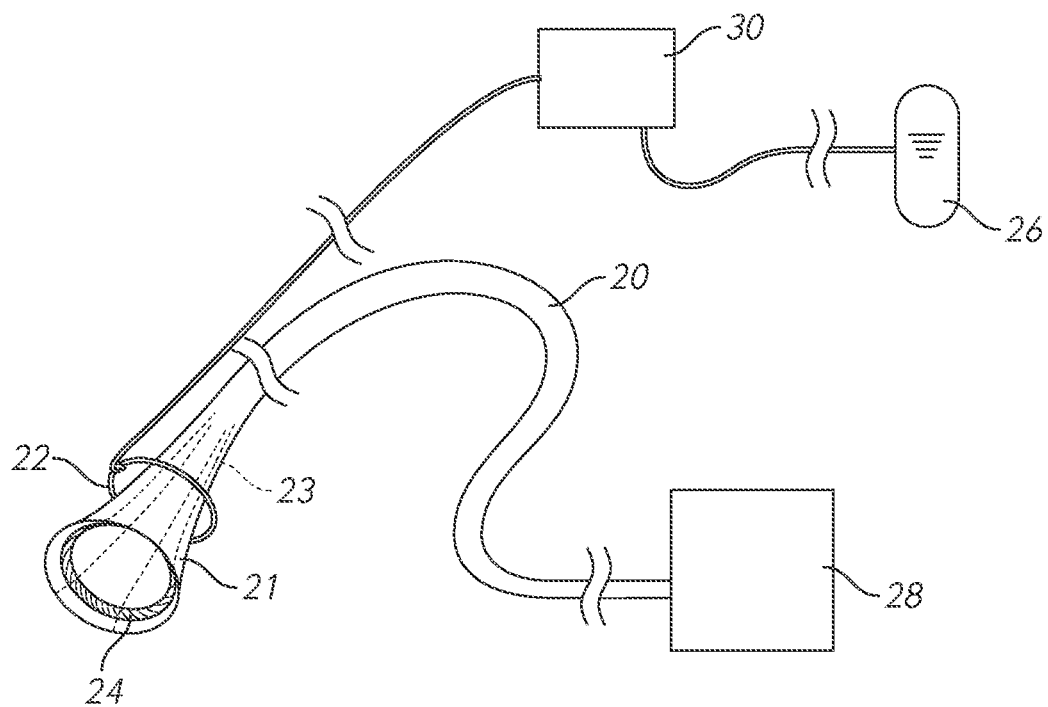
FIG. 4 illustrates an example of a device for retrieving and removing omentum tissue.

FIG. 4 shows one example of a variation of a device 20 for use as described herein. As shown, the device 20 can include an expandable distal end 21. The expandable end allows creation of a small opening in tissue to perform the procedure. Furthermore, the device 20 is coupled to a vacuum source 28 to pull tissue through the distal end 21. Accordingly, the retrieval device 20 can include one or more valves 23 (as shown in FIG. 3A) to regulate the vacuum applied through the device. As noted above, the distal end 21 can optionally compress the omentum tissue.

Alternatively, the device 20 can secure the omentum tissue so that upon withdrawal of the device 20 a strand or section of omentum is pulled along as the device is withdrawn. As also shown, the device 20 can be coupled to an energy source 30 that includes an optional ground plate 26 (for those variations that are mono-polar). In another variation, the omentum securing device 20 can include a return electrode within or about the distal end 21. In this latter variation, the presence of a return electrode 24 on the device 20 distal end 21 permits a shorter conduction path between electrodes and improves cutting and coagulation of the omentum at lower power consumption. The omentum securing device 20 can further include a vacuum pump 28 to produce suction through securing device 20 to bring tissue material into the distal end of the device. The pump can include a pressure gauge to indicate tissue contact and to allow the physician to control the force of suction delivered to the tissue.

Figure 5:
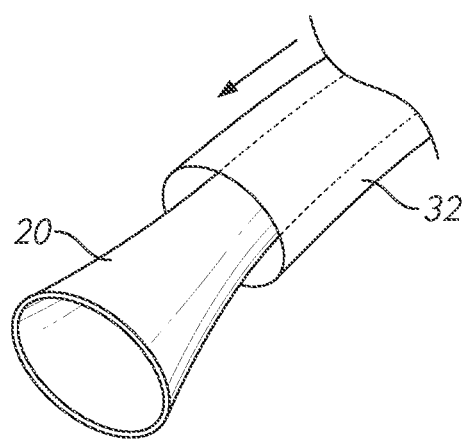
FIG. 5 illustrates a variation of a device of FIG. 4 further including a restraining conduit.

The flared end 21 of the retrieval device 20 can be self expanding. For example, the flared end 21 can include one or more shape setting splines or supports 23 located a the distal end where advancement of the distal end 21 from the endoscope causes the splines to urge outward to expand the flared end. The splines 23 can be molded as part of the distal end 21 or otherwise attached can be made out of memory metal alloy or polymer or can be structurally stiff by altering the durometer of the polymer and the shape such that when constrained, the flare is reduced and when released, the flare is spread. The device 20 can also include a restraining conduit 32 that compresses the flared end 21 by advancing distally over the flared portion as shown in FIG. 5.

Figure 6:
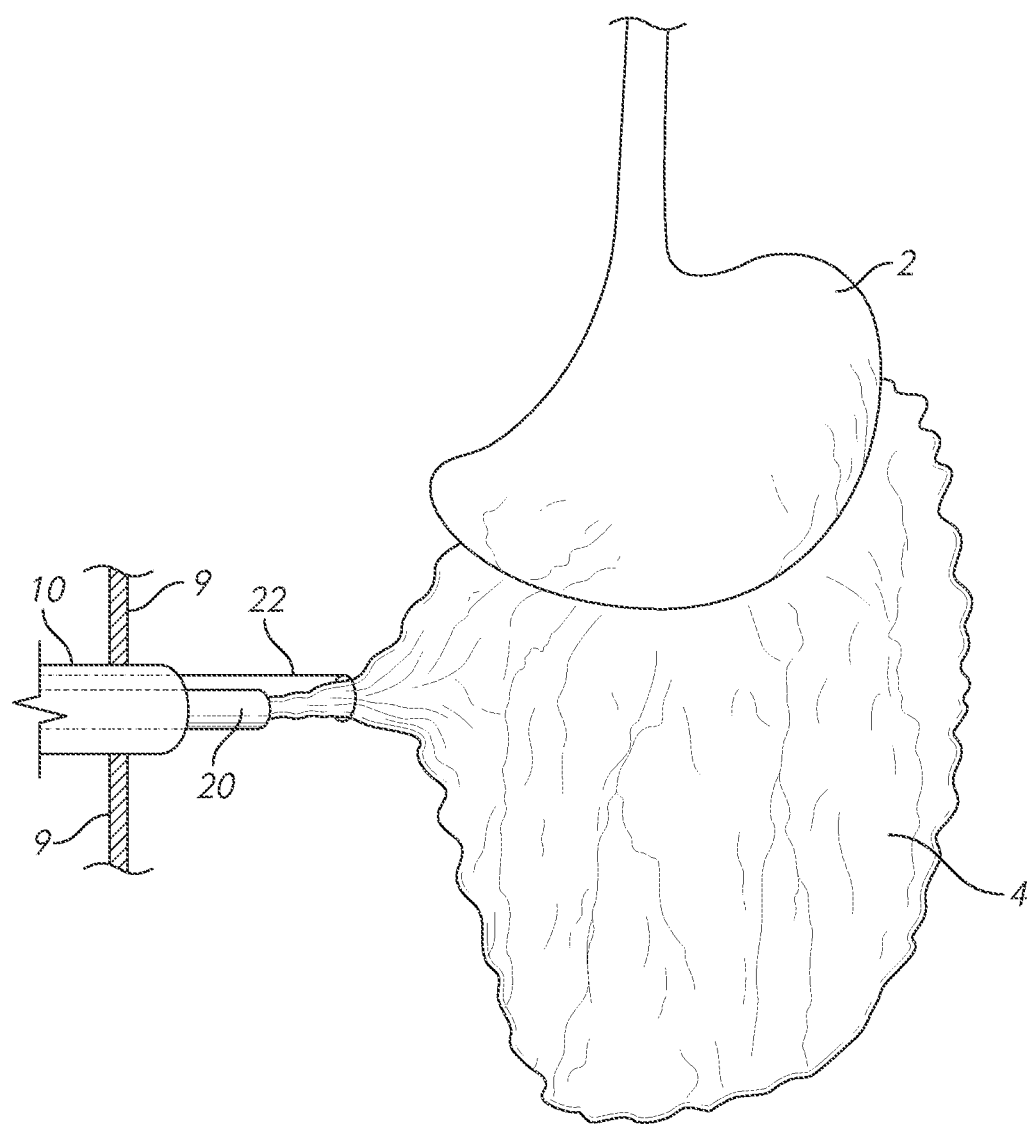
FIG. 6 illustrates a variation of removing omentum by compressing and drawing the omentum tissue within the abdominal cavity or through an abdominal wall.

FIG. 6 illustrates another variation of an omentum retrieval device 20. In this variation, the device 20 is advanced through a scope or port 10 that is placed through a wall 9 of the abdomen. The device secures the omentum tissue 4 and draws or compresses the tissue so that the secured tissue can be cut and coagulated with an electrosurgical or other device 22. The tissue debris is then removed from the body via device 20.

FIG. 7 illustrates another variation of a tissue removal device 50. In this example, the device 50 includes a shaft 60 comprising a tissue securing portion 62 located at a distal end of an elongate section 64. In some variations, the entire shaft 60 rotates either along with or independently of the tissue securing portion 62. For example, the entire shaft 60 can be coupled to the tissue securing portion 62 or the shaft can rotate but independently of the tissue securing portion 62. Permitting coupled rotation of the shaft 60 and securing portion 62 can potentially increase the ability of the device to draw or wrap tissue about the device but will increase the torque required to rotate the shaft and securing portion. Allowing the shaft to rotate independent of the securing portion 62 can lower the torque required to rotationally secure tissue about the device. Alternatively, the elongate section 64 can comprise a stationary member or rotatable member that permits for independent rotation of the tissue securing portion 62 at a distal end of the shaft. As described in further detail below, triggering of the device 50 causes tissue to become affixed to the tissue securing portion 62 while simultaneous (or closely timed) rotation of the shaft 60 causes tissue to become wrapped about or secured to the shaft 60.

The device 50 also includes a trigger or actuator 84 to initiate rotation of the tissue securing portion 62. As discussed below, actuation of the device 50 causes tissue to be secured to the tissue securing portion 62. In one example, a vacuum source V can be coupled to a vacuum port 88 on the device 50 while a valve prevents the vacuum from being applied through the device 50. In one variation, actuation of the trigger 84 can open the valve within the device 50 to cause vacuum to be drawn through the device 50 and through a distal opening 66 of the tissue securing section 62 before or just prior to rotation. The trigger 84 further causes rotation of the shaft 80 and/or the tissue securing portion 62. Accordingly, in most cases, the vacuum causes tissue to temporarily affix to the tissue securing portion 62 and rotation causes omental tissue to be wrapped or otherwise secured or wound about the tissue securing portion 62 and/or elongate portion 64. The variation of the device 50 depicted in FIG. 7A also includes a reset mechanism 86 as discussed further below.

The device 50 can include a tissue cutting section 70 that is used to separate tissue from the body, typically after the tissue is engaged with the tissue securing portion 62 (e.g., either secured to the tissue securing portion 62 or wrapped about a portion of the shaft 60). In the illustrated variation, the tissue cutting device 70 comprises a loop electrode that is axially moveable along the shaft 60. Although any number of mechanisms can be used to advance the cutting device 70 along the shaft 60, the illustrated variation includes a positioning knob 72 that is advanceable along a slot 82 in a housing 80 of the device 50 to advance the tissue cutting member 70. After sufficient advancement of the position control knob 72 and shaft body 78, the loop wire 74 can be enlarged or reduced in diameter actuation (e.g., through rotation or linear movement) of a handle 76 that is attached to the loop wire 74. The device can also include one or more fittings to couple the loop 74 to an energy supply source. Such energy supply sources include sources of RF energy, electrical power supply, coherent light, incoherent light, compressed gas, cooling fluid Although one variation of the device includes a tissue cutting section 70 comprising a loop electrode (such as an RF electrode), the tissue cutting section 70 can consist of any number of tissue cutting modalities. For example, in an additional variation, the loop electrode illustrated above can be replaced or supplemented with a snare that mechanically severs tissue. Alternatively, or in combination, the loop wire 74 can comprise a resistive heating coil or microwave antenna that perform coagulation of tissue or provides other therapeutic energy to the tissue.

Figure 7A:
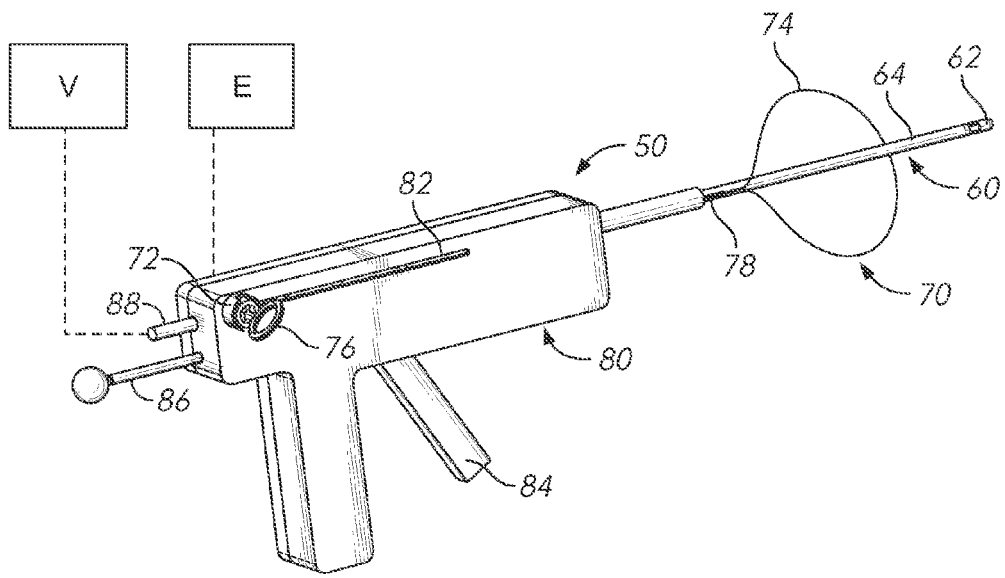
FIG. 7A shows another omentum removal device for use in the methods and procedures described herein.
Figure 7B:
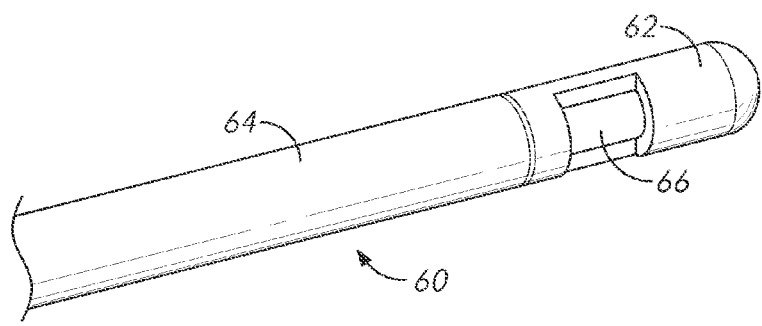
FIG. 7B illustrates a working end of the device of FIG. 7A.

FIG. 7B illustrates a distal end of the device 50 of FIG. 7A. As shown the tissue securing portion 62 includes at least one opening 66 that secures tissue during subsequent rotation of the tissue securing portion 62 or elongate section 64 of the shaft 60. Clearly, any number of openings are within the scope of the variations of the device. Devices according to the present disclosure can include alternate or additional means to secure tissue. For example, in some variations, a device 66 can employ a pinching or jaw mechanism such that the opposing sides of mechanism in the tissue securing member 62 clamp or bite tissue.

Figure 8A:
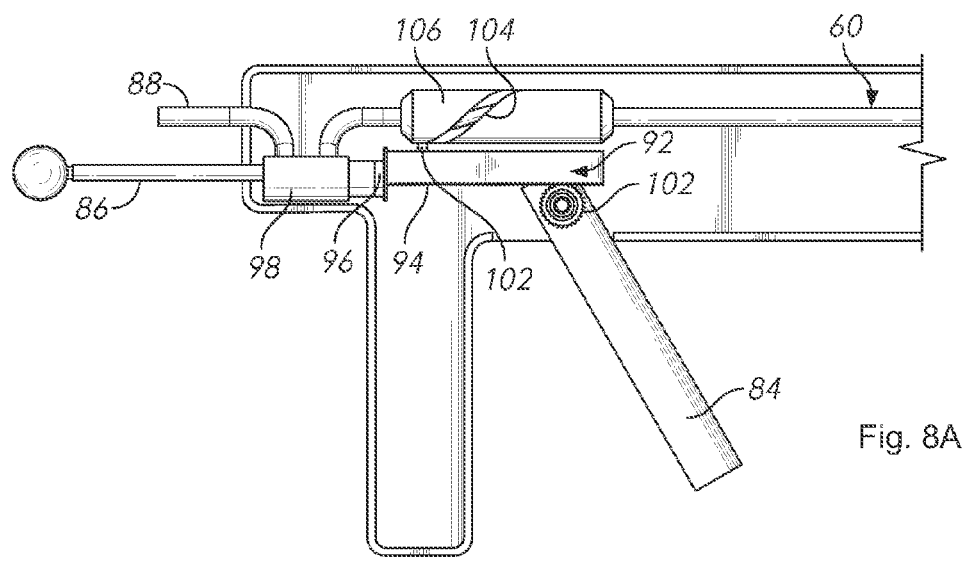
FIGS. 8A and 8B show a side view of one variation of the internal mechanisms of an omentum removal device.

As noted above, one variation of a device 50 for removal of tissue secures tissue to or about the opening 66 (or to the appropriate tissue securing mechanism discussed above). Once the tissue is affixed (e.g., temporarily or permanently) to the tissue securing portion 62, the tissue securing portion rotates (though the rotation can begin contemporaneously with securing of tissue to the tissue securing portion 62. FIG. 8A shows a partial view of the internal mechanism of the device variation depicted in FIG. 7A. The device 50 is in a non-actuated position where a rack 92 is in a rearmost position, which closes a switch 96 on a valve 98 that is coupled to a vacuum source (not shown). Closure of the switch 96 halts the flow of the vacuum that is applied through the vacuum port 88. The rack 92 is coupled to a geared assembly 102 on the trigger 84. The geared assembly 102 can comprise a pinion assembly that interacts with a geared or tooth surface on the rack 92. The pinion assembly can be coupled to the trigger 84 using a one way ratchet bearing. Accordingly, the trigger 84 can be having a number of times to drawn the rack 92 in a distal direction (the trigger can optionally be spring biased to return to the resting state shown in FIG. 8A). The rack 92 also includes a driving member or pin 102 that moves in a distal direction with the rack 92. This linear movement is causes rotation of the shaft 60 since the driving pin 102 is coupled to a spiral channel 104 on a follower shaft 106. The follower shaft is coupled to the tissue securing portion (see 62 in FIG. 7A) to cause rotation of the tissue securing portion and//or rotation of the entire shaft.

Figure 8B:
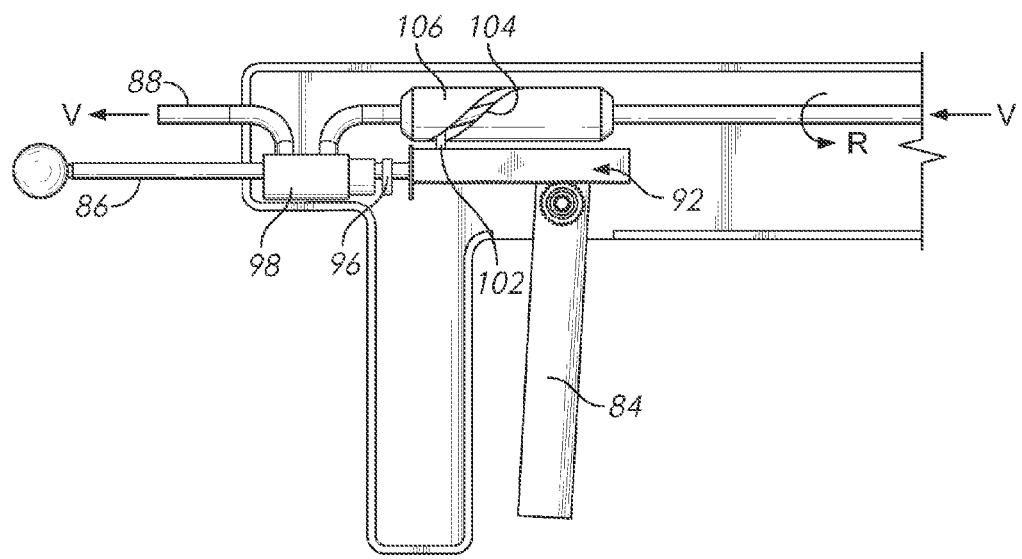

As shown in FIG. 8B, movement of the actuator 84 causes a dual effect. As shown, when the actuator 84 advances the rack 92 the switch 96 opens to permit a vacuum (V) to be drawn through the vacuum port 88, the vacuum port 88 is fluidly coupled to the tissue securing portion (preferably through to one or more openings as discussed above). Movement of the rack 92 also causes movement of the driving pin 102. Because the driving pin 102 is placed within the channel 104 of the follower shaft 106, movement of the pin 102 causes rotation R of the follower shaft 106. The rate of rotation can be adjusted by configuring the angle of the spiral channel 104. In some variations, the spiral channel is a helical channel. In alternate variations, the angle of the channel 104 is not uniform, which permits a varying degree of rotation depending on the location of the pin 102. Moreover, a delay in rotation of the following shaft 106 can be accommodated by fabricating the channel 104 to have linear portion at a proximal end of the follower shaft 106. As a result, the follower shaft 106 will not rotate so long as the pin 102 remains in the linear portion of the channel 104. FIGS. 8A and 8B are shown without the loop and snare mechanism for purposes of clarity.

Once an operator rotates the tissue securing portion to wrap a sufficient amount of tissue about the tissue securing portion 62, the rack 92 can be retracted using the reset mechanism 86. However, alternate modes can be used to reset the device (e.g., a spring loaded return, a servo-motor, a fluid piston, etc.) In any case, return of the rack 92 closes the switch 96 on the valve 98 to prevent the vacuum V from passing through the device.

FIGS. 9A to FIG. 9E illustrate an example of use of the device described in FIGS. 7A. The device 50 can be inserted through a trocar, port, or other minimcally invasive incision. In other variations, the device can be inserted through the stomach as discussed above. Accordingly, some variations of the device will include flexible shafts 60 that permit navigation through the mouth, esophagus, and stomach, yet still allow for rotation of the tissue securing portion 62. Alternatively, the device can be used during an open procedure.

FIG. 9A illustrates the shaft 60 of the device 50 inserted to position the tissue securing portion 62 and opening 66 adjacent to or within omental tissue 4. Clearly, variations of the device include a radiopaque shaft 60 and/or radiopaque markers to allow for positioning of the shaft as desired.

Figure 9B:
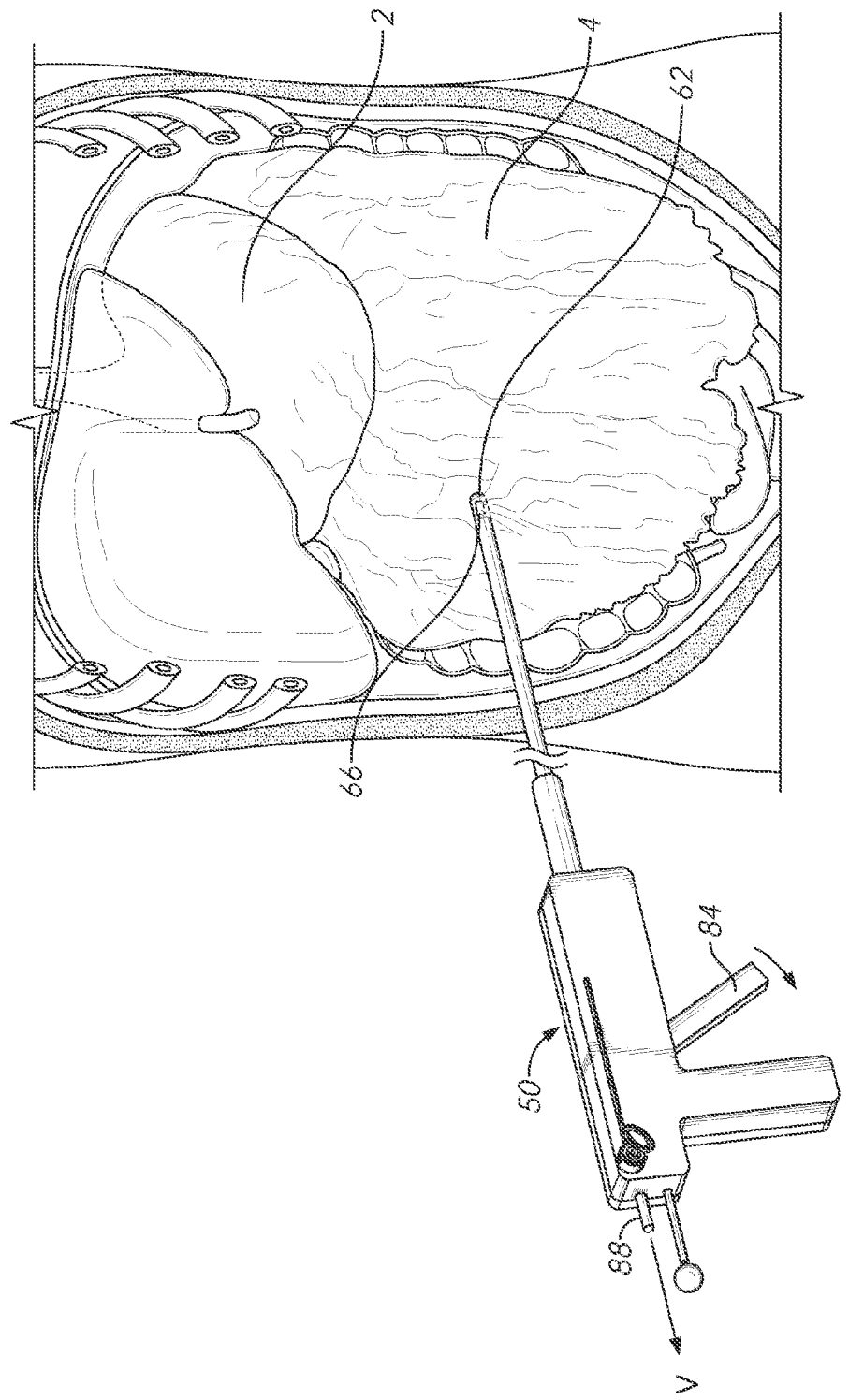

FIG. 9B illustrates actuation of the device 50 by pulling the trigger 84. As noted above, actuating the trigger 84 starts suction or creation of a vacuum in vacuum ports 88 within the device 50. The vacuum V causes tissue to enter the opening 66 in the shaft 60 such that the omental tissue becomes temporarily affixed to or about the tissue securing portion 62. In certain variations, rotation of the tissue securing portion 62 occurs subsequent to temporarily affixing the tissue to the device 50. In other variations, rotation of the shaft 60 and/or tissue securing portion 62 occurs simultaneously with the application of the vacuum V. Again, the present variation provides one method of securing tissue to the device 50. The methods described herein contemplate that tissue can be secured to the device 50 through a number of means (e.g., jaws, hooks, clamps, etc.) As shown, a visualization device 40 can be introduced adjacent to the target site. Alternatively, the visualization device 40 can be integrated or coupled to the omentum removal device 50.

Figure 9C:
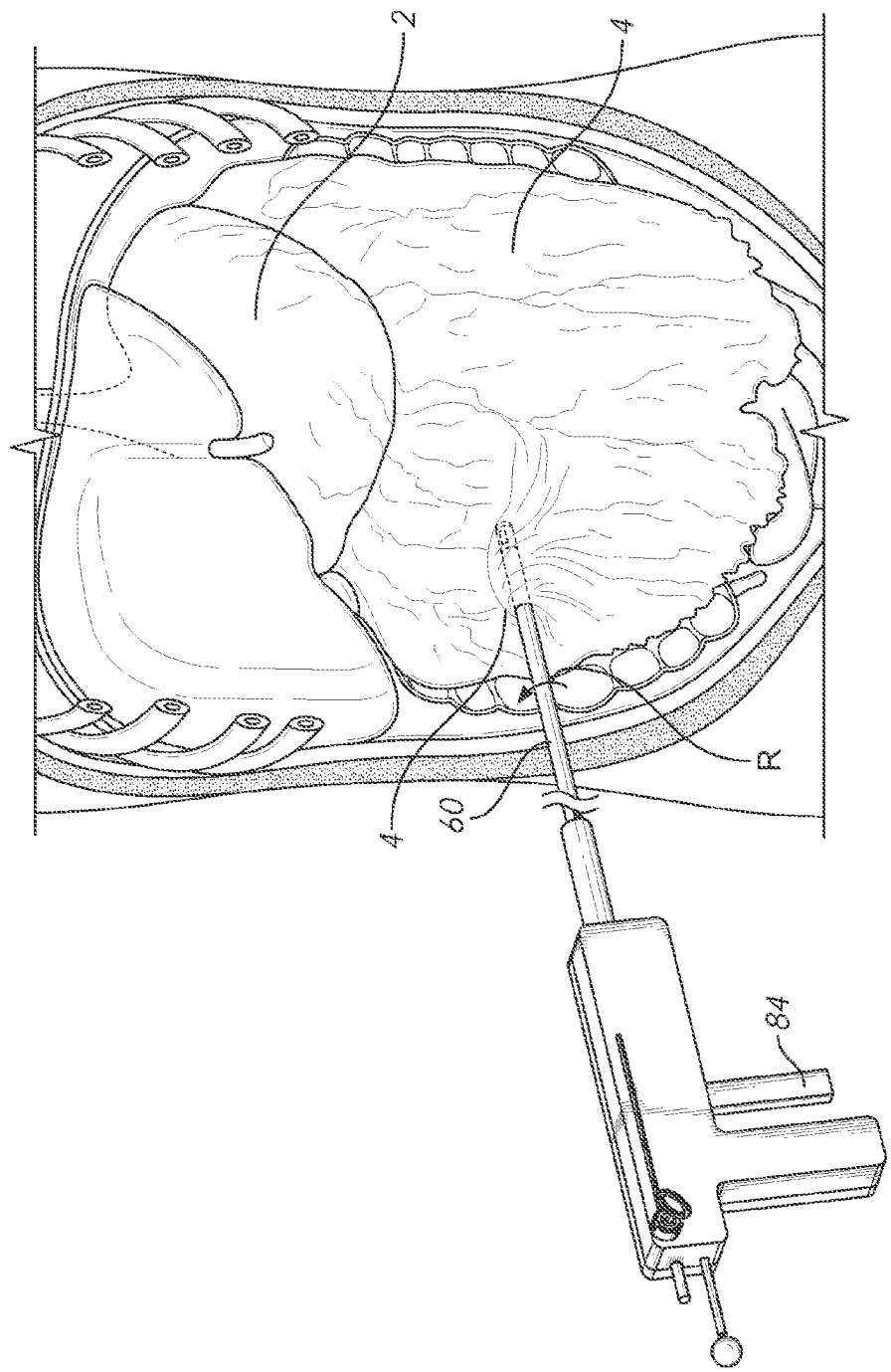
Figure 9D:
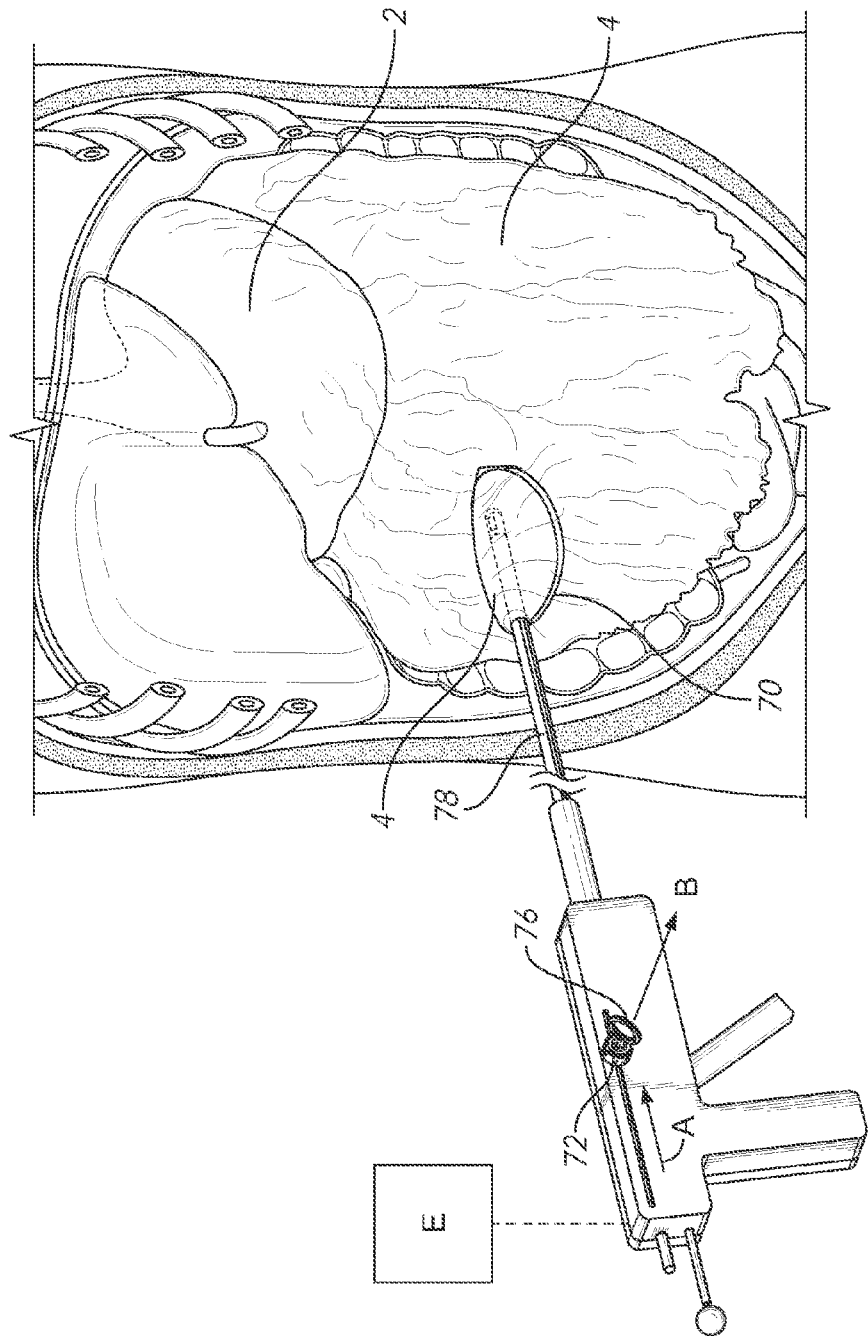

FIG. 9C illustrates rotation R of the shaft 60 and/or tissue securing portion so that omental tissue 4 wraps about the shaft 60. The omental tissue can be partially wound about the shaft or can be wound more than once around the shaft 60. Once the operator secures a sufficient amount of tissue 4 about the shaft 60, the operator then advances a position control knob 72 as shown by arrow A. Movement of the knob 72 advances a shaft body 78 and/or snare 70 to separate the omentum tissue 4 from the patient's body. Separation of the tissue 4 can occur as the snare 70 advances distally or as the snare 70 moves proximally (in the latter case the snare 70 is positioned over the tissue when advanced distally and then separates the tissue. Once the snare 70 is properly positioned, the operator can effect cutting of the tissue by actuating the snare. In some variations the snare 70 includes a snare handle 72 that, when pulled in direction B, reduces the diameter of the snare 70. As noted above, the snare 70 can mechanically sever the tissue or can employ any number of energy modes to assist in separating the tissue from the body (e.g., RF energy, coherent light, incoherent light, resistive heat, compressed gas, cooling fluid.) In another variation, the shaft or a portion thereof can have one or more electrodes to apply energy to the omentum tissue to coagulate the severed tissue and reduce or stop bleeding. In such a case, the electrodes are coupled to a power supply E. As noted above, the wrapped omentum tissue can be placed in a state of traction by continued rotation of the tissue securing portion during cutting or by withdrawing the device.

Figure 9E:
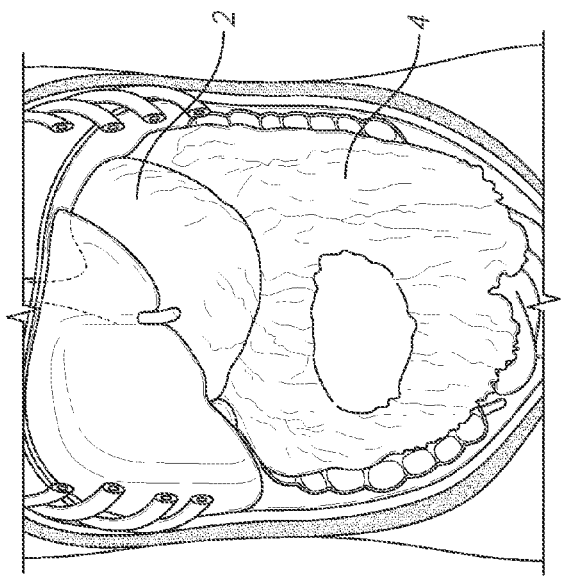
Figure 9E:
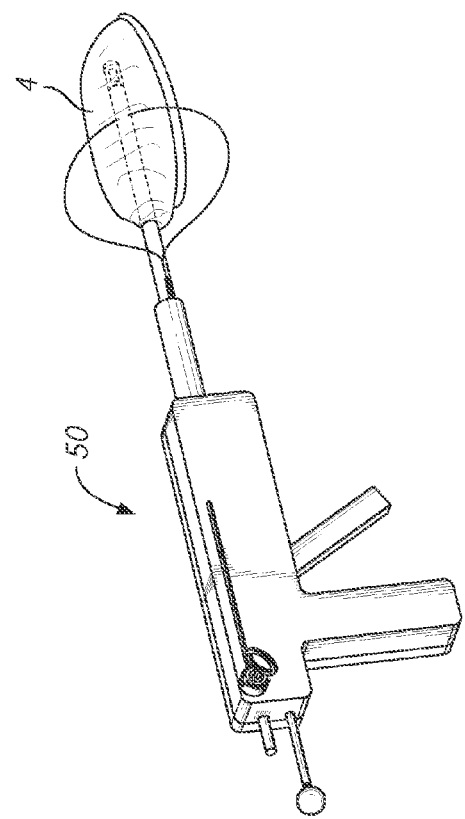

FIG. 9E illustrates removal of the omentum tissue 4 from the body as it remains wound about the shaft 60 of the device 50 until removed by the operator.

What is claimed is:

1. A method of removing a portion of omentum tissue from a human body, the method comprising:
   securing the omentum tissue to a shaft;
   rotating the shaft to affix a portion of omentum tissue about the shaft;
   separating the omentum tissue from the human body while the portion of the omentum tissue is affixed to the shaft;
   applying energy to the portion of omentum tissue to cauterize or coagulate the portion of omentum tissue to reduce bleeding; and removing the portion of omentum tissue from the body.

2. The method of claim 1, where securing the omentum tissue to the shaft comprises drawing a vacuum through an opening in the shaft to temporarily secure the omentum tissue about the opening.

3. The method of claim 1, further comprising creating an incision in the body and where removing the portion of omentum from the body comprises removing the portion of the omentum through the incision.

4. The method of claim 1, where applying energy to the portion of omentum tissue comprises advancing a loop electrode around the portion of omentum tissue and energizing the loop electrode to separate the omentum tissue.

5. The method of claim 1, where applying energy comprises applying an energy source selected from the group consisting of RF energy, coherent light, incoherent light, and resistive heat.

6. The method of claim 1, where securing the omentum tissue to the shaft occurs as the shaft beings rotating.

7. The method of claim 1, where rotating, the shaft causes a vacuum source to draw a vacuum through an opening in the shaft to pull the omentum tissue within the opening.

8. The method of claim 1, further comprising advancing an access device into a stomach of the body, creating an incision in the stomach and removing the portion of omentum from the body through the incision.

9. The method of claim 1, further comprising creating an incision in an abdominal wall and removing the portion of omentum from the incision in the abdominal wall.

10. The method of claim 1, further comprising placing a visualizing, device into the abdominal cavity.

11. The method of claim 1, further comprising morselizing the portion of omentum tissue after or during separating the omentum tissue from the body.

12. The method of claim 1, where separating the omentum tissue is performed by a process selected from the group consisting of heating, mechanically cutting and electrically cutting the portion of tissue.

13. The method of claim 1, where rotating the shaft to affix the portion of omentum tissue about the shaft further includes placing the portion of omentum tissue in a state of traction.

14. The method of claim 1, where removing the separated portion of omentum tissue from the body comprises applying a vacuum to the portion of omentum tissue.

15. The method of claim 1, where securing the portion of omentum tissue comprises advancing a retrieval device through the incision, where the retrieval device comprises a distal end, securing the portion of omentum tissue to the distal end and at least partially drawing the portion of omentum tissue into the distal end.

16. The method of claim 15, further advancing an electrosurgical component over the drawn portion of omentum tissue and applying the energy through the electrosurgical component to the portion of omentum tissue.

17. The method of claim 15, further comprising applying a vacuum through the retrieval device to secure the portion of omentum tissue to the distal end.

18. The method of claim 17, where the retrieval device farther includes a valve, and where applying the vacuum through the retrieval device further comprising actuating the valve to apply the vacuum.

19. The method of claim 1, where the incision is made in an organ selected from the group consisting of the colon, uterus, small intestine and large intestine.

20. The method of claim 1, further comprising removing abdominal fat, visceral fat, and abnormal tissue through the incision.

21. The method of claim 1, wherein separating the omentum tissue and cauterizing or coagulating the omentum tissue occurs simultaneously.

\* \* \* \* \*